United States Patent
Zhu et al.

(10) Patent No.: US 8,361,773 B2
(45) Date of Patent: Jan. 29, 2013

(54) POLYNUCLEOTIDES ENCODING POLYPEPTIDES AND HOST CELLS THEREFOR

(75) Inventors: Zhenyu Zhu, Beverly, MA (US); Jack S. Benner, II, South Hamilton, MA (US); Shuang-Yong Xu, Lexington, MA (US)

(73) Assignee: New England Biolabs, Inc., Ipswich, MA (US)

( * ) Notice: Subject to any disclaimer, the term of this patent is extended or adjusted under 35 U.S.C. 154(b) by 678 days.

(21) Appl. No.: 12/297,097

(22) PCT Filed: Mar. 30, 2007

(86) PCT No.: PCT/US2007/008312
§ 371 (c)(1),
(2), (4) Date: Oct. 14, 2008

(87) PCT Pub. No.: WO2007/120541
PCT Pub. Date: Oct. 25, 2007

(65) Prior Publication Data
US 2009/0280528 A1   Nov. 12, 2009

Related U.S. Application Data

(60) Provisional application No. 60/791,968, filed on Apr. 14, 2006.

(51) Int. Cl.
*C07H 21/00* (2006.01)
*C12P 21/00* (2006.01)
*C12N 1/21* (2006.01)
*C12N 5/10* (2006.01)
*C12N 15/00* (2006.01)
*C12N 9/16* (2006.01)
*C07K 14/00* (2006.01)

(52) U.S. Cl. .... 435/196; 435/69.1; 435/325; 435/252.3; 435/320.1; 536/23.2; 530/350

(58) Field of Classification Search ................ 435/196, 435/320.1, 325, 252.3, 69; 530/350; 536/23.2
See application file for complete search history.

(56) References Cited

U.S. PATENT DOCUMENTS
5,200,333 A    4/1993   Wilson

FOREIGN PATENT DOCUMENTS
WO       2007/097778 A2    8/2007

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Guo et al.; PNAS 101(25):9205-9210, 2004.*
European Search Report for EP07754778.4, dated Apr. 2, 2009.
Roberts, Vincze, Posfai and Macelis, Nucl. Acids Res. 33:D230-D232 (2005).
Roberts, R. J., Nucleic Acid Research 10:r117-r144 (1982).
Rebase®, <http://rebase.neb.com/rebase>, Nov. 20, 2008.

* cited by examiner

*Primary Examiner* — Delia Ramirez
(74) *Attorney, Agent, or Firm* — New England Biolabs, Inc; Harriet M. Strimpel

(57) ABSTRACT

Recombinant DNA encoding NruI- and SboI-like restriction endonucleases and methylases and their amino acid sequences are provided as well as methods for expressing the enzymes in transformed host cells and purifying the enzymes.

9 Claims, 12 Drawing Sheets

Percent Similarity: 55.147    Percent Identity: 46.324

Match display thresholds for the alignment(s):
     | = IDENTITY   : =   2     . =   1

NruI    4 LEDWDLSYDEINELLTDNPSLRSFVMGYAAEIKCRNMFFVDHPHITNIYK 53 (SEQ ID NO:3)
          || |::| :.: :|. ||||| ::|| || |  :|  |  :  : |
SboI3I  7 LERWEISEEKLTDLVDKNPSLRGMILGYVAEDKFHELFLEDE.RVKEVSK 55 ($EQ ID NO:4)

NruI   54 PDDHDRTEKGDWIINYKGHRIGVEVKSLQTNSLRLRRDGSVRPNYQCDAS 103
          ||||| .|||   ||| : ||||||||  : ||.     | ||
SboI3I 56 DDDHDRKKKGDRTFIYKGKKFTVEVKSLQTAMCKKNEDGTYSGKAQVDGS 105

NruI  104 DARTVIFADGSEVHTTALLVGEFDVVAVNIHAFENKW 140
          | | | | ||..|| || ||||..||| || |
SboI3I 106 DRRIVKFPDNSELNTTLLLKGEFDLLAVNCFAFGEGW 142

Figure 1

NruI    350..1009 nruIR
M.NruI 1347..2150 nruIM

Figure 3A-1 (SEQ ID NOS:5 AND 6)

```
          GTGACTGAGCCCAAGCGACGTGTTGCCAAAGGTGTCTCTACAACGGATGTTGTCCTTAGC
  1       ----------+----------+----------+----------+----------+----------+   60
            M  T  E  P  K  R  R  V  A  K  G  V  S  T  T  D  V  V  L  S
          TCATCCGTCGGTGACAATGCCCCGGTCTTCGTGGACATCCTCCGGCTTTTCGTACCCGTC
 61       ----------+----------+----------+----------+----------+----------+  120
           S  S  V  G  D  N  A  P  V  F  V  D  I  L  R  L  F  V  P  V
          GGGTCGACGATTGCTGATGTCACGTGGGGCAAGGGCGCTTTTTGGCGAGCGGTACCGGAG
121       ----------+----------+----------+----------+----------+----------+  180
           G  S  T  I  A  D  V  T  W  G  K  G  A  F  W  R  A  V  P  E
          GGTCTATACAAGGTACTCGCCACGGACATTCAGATGGGAGTGGATTGCAGAGACCTCCCG
181       ----------+----------+----------+----------+----------+----------+  240
           G  L  Y  K  V  L  A  T  D  I  Q  M  G  V  D  C  R  D  L  P
          TATGACGACGGCTCCGTCGATGCACTCGTGCTCGACCCTCCCTACATGGAGGGATTGTTC
241       ----------+----------+----------+----------+----------+----------+  300
           Y  D  D  G  S  V  D  A  L  V  L  D  P  P  Y  M  E  G  L  F
          CGTAAAGAGTCATCCCACATGGCGGGTGGCGGGAGCCACGGAGCATTCCGAGAGCGCTAT
301       ----------+----------+----------+----------+----------+----------+  360
           R  K  E  S  S  H  M  A  G  G  G  S  H  G  A  F  R  E  R  Y
          AGCAACTCCGCGGCGACTCCTGAGGTCGAAGGAGCTCCGAAGTATCACGATGCTGTTCTT
361       ----------+----------+----------+----------+----------+----------+  420
           S  N  S  A  A  T  P  E  V  E  G  A  P  K  Y  H  D  A  V  L
          GATCTTTACCTGAAGGCTGGTGAAGAAGCTAAGCGCGTCCTCCGCAACTACGGCGTGTTT
421       ----------+----------+----------+----------+----------+----------+  480
           D  L  Y  L  K  A  G  E  E  A  K  R  V  L  R  N  Y  G  V  F
          ATTGTGAAGTGCCAGGATGAGGTGTCGGCCAACCGTCAAAGGTTGACCCATATCGAACTC
481       ----------+----------+----------+----------+----------+----------+  540
           I  V  K  C  Q  D  E  V  S  A  N  R  Q  R  L  T  H  I  E  L
```

Figure 3A-2

```
      TACAACGCCTGGGAGAAGGACTTCTATTGTAAGGATCTTTTCGTAGTTACCAGAGCCAAC
541   ---------+---------+---------+---------+---------+---------+   600
       Y  N  A  W  E  K  D  F  Y  C  K  D  L  F  V  V  T  R  A  N
      CGGCCGGGAGTGTCCCGCCTACTAAAGCAAGAGCATGCTCGTAAAAATCACAGTTACTTT
601   ---------+---------+---------+---------+---------+---------+   660
       R  P  G  V  S  R  L  L  K  Q  E  H  A  R  K  N  H  S  Y  F
      ATGATTTTTATCAAGCGGAACCCCGAATATCCCAAGAGGATTCGGCCGACCGCAAAGGAG
661   ---------+---------+---------+---------+---------+---------+   720
       M  I  F  I  K  R  N  P  E  Y  P  K  R  I  R  P  T  A  K  E
      GCTAAGCTTCTGGGCCTCGACAACCCGAAGCCGTGGCCGTCCTCAGTGCTGCTGACGGAA
721   ---------+---------+---------+---------+---------+---------+   780
       A  K  L  L  G  L  D  N  P  K  P  W  P  S  S  V  L  L  T  E
      GGTGACGGGGATAGTCTTTTCTAG
781   ---------+---------+----   804
       G  D  G  D  S  L  F  *
```

Figure 3B-1 (SEQ ID NOS:1 AND 2)

```
      ATGGGATTTCTTGAAGACTGGGACCTCAGCTACGACGAGATCAACGAGCTTCTCACTGAC
  1   ---------+---------+---------+---------+---------+---------+   60
       M  G  F  L  E  D  W  D  L  S  Y  D  E  I  N  E  L  L  T  D

AACCCCAGCCTTCGATCGTTCGTGATGGGGTACGCAGCGGAGATCAAGTGTCGCAACATG
 61   ---------+---------+---------+---------+---------+---------+  120
       N  P  S  L  R  S  F  V  M  G  Y  A  A  E  I  K  C  R  N  M

TTCTTCGTTGATCATCCACATATCACCAACATTTACAAGCCCGATGATCACGATCGCACT
121   ---------+---------+---------+---------+---------+---------+  180
       F  F  V  D  H  P  H  I  T  N  I  Y  K  P  D  D  H  D  R  T

GAAAAGGGCGACTGGATCATCAACTACAAGGGACACCGGATCGGGGTCGAGGTCAAGAGT
181   ---------+---------+---------+---------+---------+---------+  240
       E  K  G  D  W  I  I  N  Y  K  G  H  R  I  G  V  E  V  K  S

CTCCAGACGAACTCACTGCGGCTTCGCCGAGATGGCAGTGTCCGACCAAACTACCAGTGC
241   ---------+---------+---------+---------+---------+---------+  300
       L  Q  T  N  S  L  R  L  R  R  D  G  S  V  R  P  N  Y  Q  C

GACGCTTCGGATGCCCGCACCGTGATCTTCGCTGACGGTAGCGAAGTTCATACGACCGCT
301   ---------+---------+---------+---------+---------+---------+  360
       D  A  S  D  A  R  T  V  I  F  A  D  G  S  E  V  H  T  T  A

CTGTTGGTCGGAGAATTTGACGTAGTTGCAGTCAATATCCATGCGTTCGAAAATAAGTGG
361   ---------+---------+---------+---------+---------+---------+  420
       L  L  V  G  E  F  D  V  V  A  V  N  I  H  A  F  E  N  K  W

GATTTTGCGTTCGCTAAGAACGAGGATCTCATCACGATGGAGGGTGCGACCAGGGGCGCA
421   ---------+---------+---------+---------+---------+---------+  480
       D  F  A  F  A  K  N  E  D  L  I  T  M  E  G  A  T  R  G  A

GCGAAAGACTACACCGAACTCCAGAAACGCAATCTCATCAAGACTCTCCAACCGATGCCT
481   ---------+---------+---------+---------+---------+---------+  540
       A  K  D  Y  T  E  L  Q  K  R  N  L  I  K  T  L  Q  P  M  P
```

Figure 3B-2

```
     ATGGACGTGCCAGCCCCGTACACTCGAGATCCCTTCAAACTCTTCGACGAGATCATCGAA
541  ---------+---------+---------+---------+---------+---------+  600
      M  D  V  P  A  P  Y  T  R  D  P  F  K  L  F  D  E  I  I  E

GAGCGCATGAAGGGTGAGCAGCCTCAGCTCAAGGCGAAGATCATCGAAGACGAAGAGTGA
601  ---------+---------+---------+---------+---------+---------+  660
      E  R  M  K  G  E  Q  P  Q  L  K  A  K  I  I  E  D  E  E  *
```

Sbo13I Endonuclease Purification

Sbo13I RM 5.4 kb Plasmid Map

Figure 8 (SEQ ID NOS:7 AND 8)

```
      ATGGTGATTTTAGCAGATATTAAAATAGACGACGTAGAAGCGGAACACACTGAAATTAAA
  1   ---------+---------+---------+---------+---------+---------+  60
      M  V  I  L  A  D  I  K  I  D  D  V  E  A  E  H  T  E  I  K
      AAGAAAAAGAGAGTTCAAGGTGGTGAGGCTACGAGTAATGTAACAATGTCAGCACACCTG
 61   ---------+---------+---------+---------+---------+---------+ 120
      K  K  K  R  V  Q  G  G  E  A  T  S  N  V  T  M  S  A  H  L
      AGCGGCAACGCCGAAGTTTTCCCGCAAATCCTAGACTTGCATGTTCCTGAAGGGGCTGTG
121   ---------+---------+---------+---------+---------+---------+ 180
      S  G  N  A  E  V  F  P  Q  I  L  D  L  H  V  P  E  G  A  V
      ATTGCGGATGTCACTTTTGGTGGCGGCGTATTTTGGAAAAAAGTTAATCTTGATAAGTAC
181   ---------+---------+---------+---------+---------+---------+ 240
      I  A  D  V  T  F  G  G  G  V  F  W  K  K  V  N  L  D  K  Y
      AAGCTGTTGGCAACAGATATTGCTAACGGAGTCGATTGTCGAGATCTCCCTTATGAGGAA
241   ---------+---------+---------+---------+---------+---------+ 300
      K  L  L  A  T  D  I  A  N  G  V  D  C  R  D  L  P  Y  E  E
      ACAAGCCTTGATGCCTTAGTACTTGATCCTCCATATATGGAGGGATTACTTCGCAACAAT
301   ---------+---------+---------+---------+---------+---------+ 360
      T  S  L  D  A  L  V  L  D  P  P  Y  M  E  G  L  L  R  N  N
      GCTTCGCACAAAGCAGGGGATGGAACACATTCTACGTTCAGGAAATATTACTCTAACGGC
361   ---------+---------+---------+---------+---------+---------+ 420
      A  S  H  K  A  G  D  G  T  H  S  T  F  R  K  Y  Y  S  N  G
      GACGAAAAAAGTGTAGCGGGGGCTCCAAAATGGCATGCGGCTGTTACCGATCTTTATTAT
421   ---------+---------+---------+---------+---------+---------+ 480
      D  E  K  S  V  A  G  A  P  K  W  H  A  A  V  T  D  L  Y  Y
481   ---------+---------+---------+---------+---------+---------+ 540
      K  A  S  D  E  A  F  R  V  L  K  D  N  G  V  F  I  V  K  C
      CAAGATGAGGTTTCGGCTAACAAACAATGGTTGACTCATGTTGAAATAATAAACTATTGC
541   ---------+---------+---------+---------+---------+---------+ 600
      Q  D  E  V  S  A  N  K  Q  W  L  T  H  V  E  I  I  N  Y  C
      GAATCTCTTGGCTTCTATACTAAAGATCTTTTTGTCGTTGTTCGTAGTAACAAGGCTGGG
601   ---------+---------+---------+---------+---------+---------+ 660
      E  S  L  G  F  Y  T  K  D  L  F  V  V  V  R  S  N  K  A  G
      GTTTCTCGAATGAAGAAGCAGGTTCATGCAAGGAAGAATCACAGTTACTTCCTTGTTTTT
661   ---------+---------+---------+---------+---------+---------+ 720
      V  S  R  M  K  K  Q  V  H  A  R  K  N  H  S  Y  F  L  V  F
      ATAAAACTTCCGGAAAAGAAAAGAAAGAAGAAAACGTTATGA
721   ---------+---------+---------+---------+--  762
      I  K  L  P  E  K  K  R  K  K  K  T  L  *
```

Figure 9 (SEQ ID NOS:9 AND 10)

```
    ATGAGAGAACCCTCGATTCTAGAAAGATGGGAAATAAGCGAAGAAAAATTAACTGACTTG
1   ------------+---------+---------+---------+---------+---------+ 60
    M  R  E  P  S  I  L  E  R  W  E  I  S  E  E  K  L  T  D  L
    GTTGATAAAAACCCCTCTCTTAGAGGAATGATTTTAGGTTATGTTGCTGAGGATAAATTT
61  ------------+---------+---------+---------+---------+---------+ 120
    V  D  K  N  P  S  L  R  G  M  I  L  G  Y  V  A  E  D  K  F
    CACGAGCTATTCCTTGAAGATGAAAGAGTAAAGGAGGTTTCTAAAGACGACGATCATGAC
121 ------------+---------+---------+---------+---------+---------+ 180
    H  E  L  F  L  E  D  E  R  V  K  E  V  S  K  D  D  D  H  D
    AGAAAGAAAAAAGGAGATAGAACCTTTATTTACAAAGGTAAAAAATTTACAGTTGAAGTT
181 ------------+---------+---------+---------+---------+---------+ 240
    R  K  K  K  G  D  R  T  F  I  Y  K  G  K  K  F  T  V  E  V
    AAAAGCTTGCAAACCGCAATGTGCAAGAAAAATGAAGACGGAACTTATTCAGGAAAAGCC
241 ------------+---------+---------+---------+---------+---------+ 300
    K  S  L  Q  T  A  M  C  K  K  N  E  D  G  T  Y  S  G  K  A
    CAAGTAGACGGCAGTGATCGAAGAATAGTAAAATTCCCAGACAATTCAGAATTAAATACG
301 ------------+---------+---------+---------+---------+---------+ 360
    Q  V  D  G  S  D  R  R  I  V  K  F  P  D  N  S  E  L  N  T
    ACGTTACTCTTGAAAGGAGAGTTTGATCTATTAGCCGTTAATTGCTTTGCTTTTGGTGAA
361 ------------+---------+---------+---------+---------+---------+ 420
    T  L  L  K  G  E  F  D  L  L  A  V  N  C  F  A  F  G  E
    GGATGGAAATTTGCTTTTGCAAAAAATTCTGACCTTCCCACCTCAACATTCAAAAAATAC
421 ------------+---------+---------+---------+---------+---------+ 480
    G  W  K  F  A  F  A  K  N  S  D  L  P  T  S  T  F  K  K  Y
    ACAGAAGAACAAAGGAAACAACTTATTGCCTCACTGATTCCTGTAACTTGGCCACCAAAG
481 ------------+---------+---------+---------+---------+---------+ 540
    T  E  E  Q  R  K  Q  L  I  A  S  L  I  P  V  T  W  P  P  K
    CCACCATTCAGTGATGACCCATTCCACCTTCTGGACGAGATGATTGCAGCGCCAGAAGAG
541 ------------+---------+---------+---------+---------+---------+ 600
    P  P  F  S  D  D  P  F  H  L  L  D  E  M  I  A  A  P  E  E
    GAACCGGTGATAGAAGAAAGTAGTGAATTAAAAGAAGTAAAAGAAGATATAGATGTAGTT
601 ------------+---------+---------+---------+---------+---------+ 660
    E  P  V  I  E  E  S  S  E  L  K  E  V  K  E  D  I  D  V  V
    AAAGTGAAATCATAA
661 ---------+----- 675
    K  V  K  S  *
```

POLYNUCLEOTIDES ENCODING POLYPEPTIDES AND HOST CELLS THEREFOR

CROSS REFERENCE

This application is a §371 application of international application number PCT/US2007/008312 filed Mar. 30, 2007, which claims priority from U.S. provisional application No. 60/791,968 filed Apr. 14, 2006.

BACKGROUND OF THE INVENTION

Restriction endonucleases are enzymes that occur naturally in certain unicellular microbes—mainly bacteria and archaea—and function to protect these organisms from infections by viruses and other parasitic DNA elements. Restriction endonucleases bind to specific sequences of nucleotides ('recognition sequence') in double-stranded DNA molecules (dsDNA) and cleave the DNA, usually within or close to the sequence, generating DNA fragments of various sizes. In vivo, the restriction fragments in turn serve as the substrates for further exonuclease digestion, leading to total degradation. Restriction endonucleases commonly occur with one or more companion enzymes termed modification methyltransferases. Methyltransferases bind to the same sequences in dsDNA as the restriction endonucleases they accompany, but instead of cleaving the DNA, they alter it by the addition of a methyl group to one of the bases within the sequence. This methylation ('modification') prevents the restriction endonuclease from binding to that site thereafter, rendering the site resistant to cleavage. Methyltransferases function as cellular antidotes to the restriction endonucleases they accompany, protecting the cell's own DNA from destruction by its restriction endonucleases. Together, a restriction endonuclease and its companion modification methyltransferase(s) form a restriction-modification (R-M) system.

A large and varied number of restriction endonucleases have been classified as 'Type II' restriction endonucleases. These enzymes cleave DNA at defined positions, and in purified form can be used to cut DNA molecules into precise fragments for gene cloning and analysis. The biochemical precision of Type II restriction endonucleases far exceeds anything achievable by chemical methods, making these enzymes the reagents sine qua non of molecular biology laboratories. In this capacity, as molecular tools for gene dissection, Type II restriction endonucleases have had a profound impact on the life sciences in the past 34 years, transforming the academic and commercial arenas, alike. Their utility has spurred a continuous search for new restriction endonucleases, and a large number have been found. Today 259 Type II endonucleases specificities are known, each possessing different DNA cleavage characteristics (Roberts, Vincze, Posfai and Macelis, *Nucl. Acids Res.* 33:D230-D232 (2005)). (REBASE®, available at rebase.neb.com/rebase). Concomitantly, the production and purification of these enzymes have been improved by the cloning and over-expression of the genes that encode them in non-natural production strain host cells such as *E. coli*.

Since the various restriction enzymes appear to perform similar biological roles, in much the same ways, it might be thought that they would resemble one another closely in amino acid sequence and behavior. Experience shows this not to be true, however. Surprisingly, far from resembling one another, most Type II restriction enzymes appear unique, resembling neither other restriction enzymes nor any other known kind of protein. Type II restriction endonucleases seem to have arisen independently of one another for the most part during evolution, and to have done so hundreds of times, so that today's enzymes represent a heterogeneous collection rather than a discrete family. Some restriction endonucleases act as homodimers, some as monomers, and others as heterodimers. Some bind symmetric sequences, others asymmetric sequences; some bind continuous sequences, others discontinuous sequences; some bind unique sequences, others multiple sequences. Some are accompanied by a single methyltransferase, others by two, and yet others by none at all. When two methyltransferases are present, sometimes they are separate proteins; at other times they are fused. The orders and orientations of restriction and modification genes vary, with all possible organizations occurring. Several kinds of methyltransferases exist, some methylating adenines (m6A-MTases), others methylating cytosines at the N-4 position (m4C-MTases), or at the 5 position (m5C-MTases). Usually there is no way of predicting, a priori, which modifications will block a particular restriction endonuclease, which kind(s) of methyltransferases(s) will accompany that restriction endonuclease in any specific instance, or what their gene orders or orientations will be.

Great variability exists among restriction-modification systems. Each enzyme is unique in amino acid sequence and catalytic behavior; each occurs in unique enzymatic association, adapted to unique microbial circumstances; and each presents the experimenter with a unique challenge. Sometimes a restriction endonuclease can be cloned and over-expressed in a straightforward manner but more often than not it cannot, and what works well for one enzyme can work not at all for the next. Success with one enzyme is not a predictor of success with another.

SUMMARY OF THE INVENTION

In an embodiment of the invention, an isolated DNA is provided that encodes an NruI restriction endonuclease and has a DNA sequence sharing at least 90% sequence identity with SEQ ID NO:1.

In another embodiment of the invention, a recombinant NruI restriction endonuclease is provided that has an amino acid sequence that shares at least 45% or 80% sequence identity with SEQ ID NO:2.

In another embodiment of the invention, a vector is provided that includes a DNA segment encoding the NruI restriction endonuclease having a DNA sequence sharing at least 90% sequence identity with SEQ ID NO:1.

In another embodiment of the invention, a host cell is provided that is transformed by the vector described above. The transformed host cell may have a chromosomal DNA that is modified with Sbo13I or NruI methylase. The chromosomal DNA may also be modified with a non-cognate methylase for protecting against NruI restriction endonuclease digestion.

In another embodiment of the invention, a method is provided for producing recombinant NruI restriction endonuclease that includes culturing a host cell transformed with the vector containing a DNA segment encoding an NruI-like restriction endonuclease under conditions suitable for expression of the endonuclease.

In another embodiment of the invention, an isolated DNA is provided that encodes the SboI restriction endonuclease and has a DNA sequence having at least 90% sequence identity with SEQ ID NO:9 as well as a vector containing the DNA segment and a host cell transformed with the vector.

In another embodiment of the invention, a recombinant SboI restriction endonuclease is provided that has an amino acid sequence that shares at least 45% or 80% sequence identity with SEQ ID NO:10.

In another embodiment of the invention, a host cell is provided in which the chromosomal DNA is modified with a non-cognate methylase for protecting against SboI restriction endonuclease digestion where the host cell can be cultured under conditions suitable for expression of the endonuclease.

In another embodiment of the invention, a DNA segment having restriction endonuclease activity is provided having a sequence that shares at least 90% identity with SEQ ID NO:7. This segment can be incorporated into a vector for cloning and expressing the protein in a host cell, where the host cell is SboI methylase.

In another embodiment of the invention, a recombinant DNA methylase is provided having an amino acid sequence sharing at least 80% identity with SEQ ID NO:8.

BRIEF DESCRIPTION OF THE DRAWINGS

FIG. 1 shows the initial amino acid sequence comparison between the inverse PCR product (SEQ ID NO:3) and the Sbo13I endonuclease sequence (SEQ ID NO:4).

FIGS. 3A-1 and 3A-2 show the NruI methylase gene sequence (nruIM, 804 bp) (SEQ ID NO:5) and the encoded amino acid sequence (SEQ ID NO:6).

FIGS. 3B-1 and 3B-2 show the NruI restriction endonuclease gene sequence (nruIR, 660 bp) (SEQ ID NO: 1) and the encoded amino acid sequence (SEQ ID NO:2).

FIG. 8 shows the DNA sequence and encoded amino acid sequence of Sbo13I methylase gene (SEQ ID NOS:7 and 8, respectively).

FIG. 9 shows the DNA sequence and encoded amino acid sequence of Sbo13I restriction endonuclease gene (SEQ ID NOS:9 and 10, respectively).

DETAILED DESCRIPTION OF THE INVENTION

Figure 2:
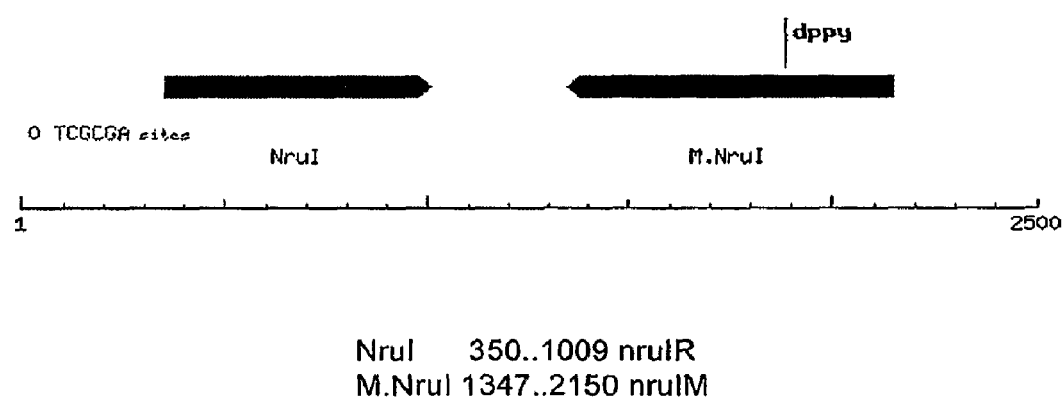
FIG. 2 shows the gene organization of the NruI R-M system. nruIR, NruI restriction endonuclease gene; nruIM, NruI methylase gene.
Figure 4:
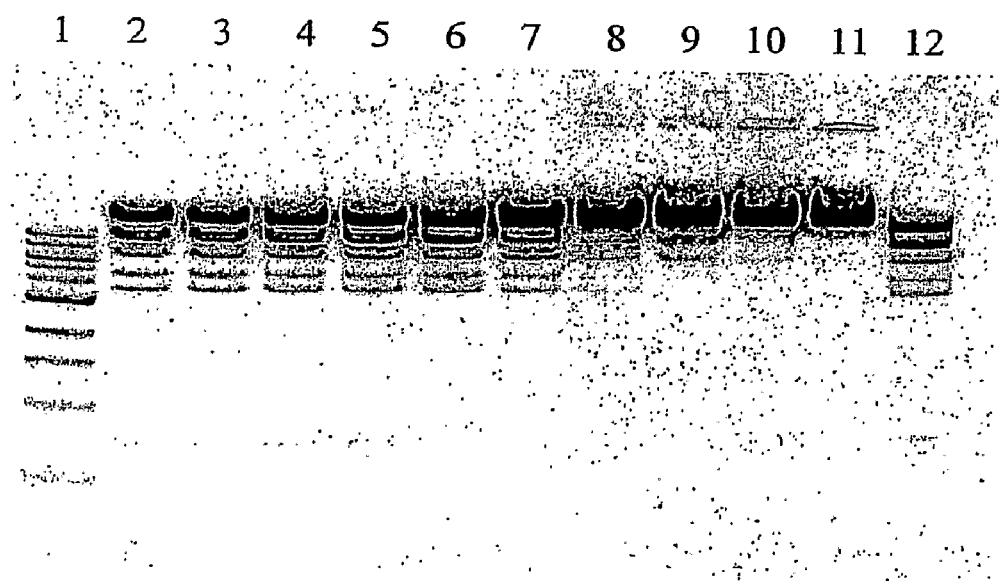
FIG. 4 shows recombinant NruI restriction endonuclease activity in cell extracts. Lambda DNA was used as the substrate. Lane 1, 1 kb DNA marker; Lanes 2-11, 3 μl 1/100, 1/200, 1/400, 1/800, 1/1600, 1/3200, 1/6400, 1/12800, 1/25600, 1/51200, diluted cell extracts added in the restriction digestions; Lane 12, Lambda DNA digested with native NruI.
Figure 5:
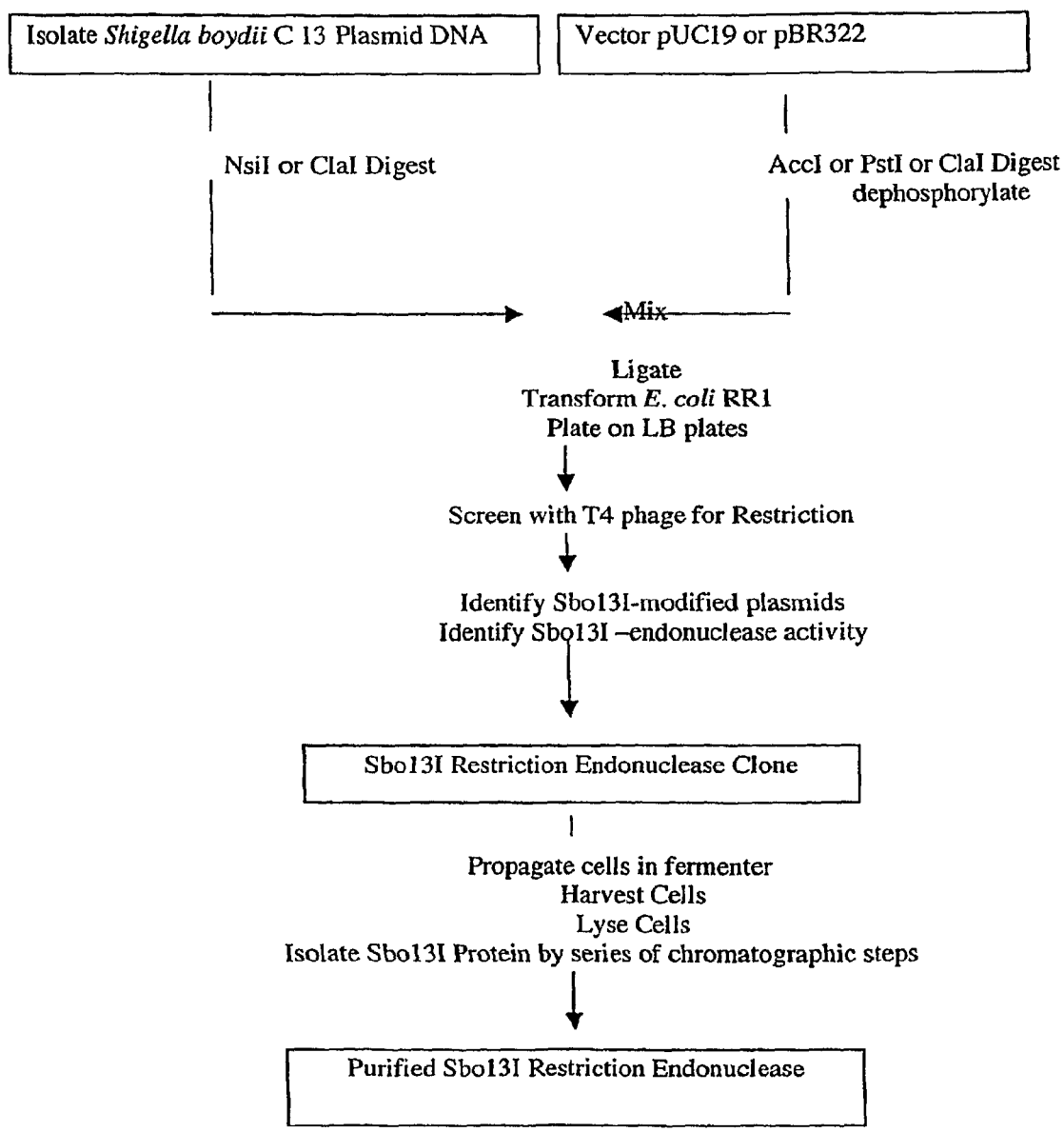
FIG. 5 illustrates the scheme for cloning the Sbo13I restriction endonuclease.

Present embodiments of the invention relate to recombinant DNA that encodes the NruI restriction endonuclease (NruI) as well as the NruI modification methyltransferase (NruI methylase; M.NruI), and the expression of NruI in *E. coli* cells that contain the recombinant DNA.

The NruI restriction endonuclease and methyltransferase are enzymes that have been isolated from the bacterium *Nocardia rubra* (Roberts, R. J., *Nucleic Acid Research* 10:r117-r144 (1982)). The NruI restriction endonuclease binds to the symmetric nucleotide (nt) sequence 5'-TCGCGA-3' in dsDNA molecules and cleaves the DNA between the G and C in each strand thus: 5'-TCG/CGA-3', producing DNA fragments with blunt ends (/ indicates the position of strand-cleavage). Many restriction endonucleases that occur in nature are accompanied by protective modification methyltransferases. However, the selection of the NruI methylase gene from the *Nocardia* rubra by expression of nruIM gene in a heterologous host was not successful. The initial NruI restriction endonuclease sequence was obtained from PCR DNA fragments amplified with degenerate primers designed from the N-terminal amino acid sequence of NruI restriction endonuclease. The identification and verification of the bona fide sequence depend on the sequence similarity to Sbo13I (an isoschizomer of NruI), whose DNA sequence has been cloned and determined, as described in this patent also. The whole NruI restriction endonuclease gene and the accompanying methylase gene were then sequenced from the inverse PCR product.

Hurdles in Cloning NruI
Unsuccessful Methylase Gene Selection

The methylase selection method described in U.S. Pat. No. 5,200,333 is the preferred approach for cloning restriction-modification systems. It was concluded that M.NruI exists because the genomic DNA from *Nocardia rubra* is resistant to the NruI digestion. However, the cloning of NruI methylase gene (nruIM) proved to be very difficult. Dozens of genomic DNA libraries were constructed with different vectors and various enzyme digested genomic DNA fragments in the period of over five years. The most recent plasmid library for the selection of nruIM was constructed using the vector pBR322 in which there is an NruI site in the Tc resistant gene. However, even there, colonies survived after the NruI challenge and the plasmids from the survivor colonies were not resistant to NruI digestion. The sequencing of the inserts did not reveal any homologous sequence to the DNA methylases.

There were potentially several reasons for this failure. These include part or all of the following:

the restriction enzymes used to construct the initial libraries cut within the methylase gene;

cloning the proper DNA fragment from the libraries failed due to the large size of the DNA fragment;

methylase gene in *E. coli* had low expression;

poor modification of NruI sites on a plasmid;

nruIR gene toxicity when nruIR gene is expressed more than nruIM gene when both genes are cloned in the same DNA fragment.

The Protein Sequencing of N-Terminus of NruI

Purified and concentrated native NruI was analyzed on SDS-PAGE. There were more than ten protein bands in the lane. The four bands between 25 kDa and 47.5 kDa were identified and selected for N-terminal sequencing. The protein band close to 27 kDa produced a protein sequence of MGFLADXDLSYDEINELLTDN (X=unidentified amino acid residue) (SEQ ID NO:11).

Inverse PCR by the Degenerate Primer from N-Terminal Sequence

Inverse PCR was performed on 22 self-ligated genomic DNA templates using a pair of primers derived from the NruI N-terminal sequence. Twenty-six amplified DNA fragments were identified in agarose gels. The DNA fragments were gel-purified and sequenced by the degenerate primers. The DNA sequence from DNA fragments #3, #16, #17 and #26 compiled into a 774-bp contig. The remaining DNA fragments formed 17 other contigs. Fortunately, the amino acid sequence translated from the latter half of the 774-bp contig shared significant sequence similarity to the amino acid sequence of Sbo13I (NruI isoschizomer), whose coding gene has been cloned and sequenced previously (see Example 2). This high degree of sequence homology identifies the correct DNA fragment encoding part of NruI A second round of inverse PCR revealed the whole sequence of NruI and the adjacent M.NruI.

Over-Expression of NruI in *E. Coli* Modified by Sbo13I Methylase

Since the methylase selection of nruIM by its expression in a heterologous host failed multiple times, it was suspected that nruIM expression in *E. coli* might be insufficient. In contrast, the methylase isoschizomer, M.Sbo13I, has been shown to express at a high level and to be fully active in *E. coli*. The plasmid pACYC-sbo13IM was constructed by ligation of the PCR fragment to pACYC184 and transformed into *E. Coli* host ER2683. The assumed NruI restriction endonuclease gene was amplified in PCR, digested with restriction enzymes and ligated to pUC19 with compatible ends. The ligated plasmid was transformed into premodified host ER2683 [pACYC-sbo13IM]. Colonies were picked and grown in LB with Amp and Chloramphenical (Cm) in 4 ml culture overnight. The sonicated cell extracts from 24 samples were tested for endonuclease activity on lambda DNA. Eight out of 24 cultures displayed high NruI restriction endonuclease activity. This gene was thus confirmed to be the nruIR gene. The insert in three clones (#10, #14, and #15) was sequenced. All of them were confirmed to be the wild-type nruIR gene, and clone #14 was deposited in the NEB strain collection (New England Biolabs, Inc., (NEB), Ipswich, Mass.). The strain was then tested for stability in large cultures and found to be stable. The recombinant NruI was over-expressed at the level of $6.5 \times 10^6$ units per gram of wet cells.

In summary, an expression strategy was ultimately developed which overcame a number of hurdles and ultimately proved successful in yielding an NruI over-expression clone. This strategy relied on the expression of M.Sbo13I to protect host DNA against NruI digestion.

The method described herein by which the nruIM and nruIR genes can be cloned and expressed in *E. coli* is described in detail in Example I.

All references cited above and below as well as U.S. provisional application Ser. No. 60/791,968 filed Apr. 14, 2006 are herein incorporated by reference.

EXAMPLES

Example 1

Cloning of NruI Restriction-Modification System in *E. coli*

1. Preparation of Genomic DNA

Genomic DNA was prepared from 10 g of *Nocardia rubra*, by the following steps:

a. 10 grams of cell paste were suspended in 35 ml of 0.1M Tris-HCl, 0.1M EDTA, pH 7.

b. 25 ml of 2 mg/ml fresh lysozyme in 0.1M Tris-HCl, 0.1 MEDTA, pH 7.6 were added to (a) and incubated at 37° C. for 1 hour.

c. Protease K was added to (b) to a final volume of 0.1 mg/ml and incubated at 37° C. for 1 hour.

d. SDS to 0.1% (6 ml of 10% stock) and 6 ml of 8% sarcosyl solution were added to the lysate and incubated at 55° C. for 1 hour.

e. A Phenol-$CHCl_3$ extraction was performed 3 times and a $CHCl_3$ extraction was performed two times.

f. DNA was dialyzed in 4 L 10 mM Tris-HCl, pH 7.5, 0.1 mM EDTA at 4° C., and the buffer changed twice.

g. 0.5 ml of RNaseA (1 mM) was added and incubated at 37° C. for 1 hour.

h. 30 µl of DNA was analyzed on a 0.80% agarose gel. This procedure produced 5 mg genomic DNA. The size of the genomic DNA was much larger than 10 kb on gel.

2. Purification of Native NruI

Native NruI was purified from *Nocardia rubra* by the AKTA FPLC P-900 (GE Health, Piscataway, N.J.). Five hundred grams of cells were broken by French Press and the lysate was purified by the following columns: heparin hyper-D, Source Q, Affigel blue, ceramic HTP and Mono Q column. The total units in crude extract were $5.6 \times 10^6$ units, and the final purified enzymes were $1.5 \times 10^6$ units. The enzyme preparation was functionally pure, free of DNA, RNA and other nonspecific nucleases.

3. N-Terminal Sequencing of Native NruI

The purified NruI restriction endonuclease was subjected to electrophoresis on 4-20% Tris-Glycine SDS-PAGE. There were more than ten protein bands identified in the SDS-PAG. The four bands between 25 kDa and 47.5 kDa were selected and their N-terminus amino acid sequences were determined by the Edman degradation method. Only the protein band close to 27 kDa produced a protein sequence of MGFLADXDLSYDEINELLTDN (X=unidentified amino acid residue) (SEQ ID NO:11). The rest of the protein bands did not yield meaningful data.

4. Preparation of Genomic DNA and Construction of NruI Genomic DNA Library for Inverse PCR Genomic DNA was prepared from *Nocardia rubra* by phenol-chloroform extractions. One µg of genomic DNA was digested with AluI, ApaI, ApoI, BfaI, BsaAI, BsaHI, BsaWI, BssHII, BstYI, CviAII, EagI, HaeII, HhaI, HincII, HpyCH4IV, HpyCH4V, MseI, NspI, RsaI, SfoI, SmaI, and Tsp509I, respectively. Digested DNA was then purified by spin column and self-ligated at 2 ng/µl concentration using NEB's quick-ligation kit. After ligation, the DNA was purified again by spin column. The final volume was 50 µl and 10 µl was used as the template for degenerate inverse PCR.

5. Degenerate Inverse PCR

PCR primers were designed from the N-terminal NruI protein sequence. The following primers were made:

```
                                          (SEQ ID NO: 12)
5RTCNGCYAARAANCCCA  (R = A, G; N = A, T, C, G; Y =

T, C; 5 = Phosphate) (331-270)

(SEQ ID NO: 13)
5RTCNGCNAGTAANCCCA  (R = A, G; N = A, T, C, G; Y =

T, C; 5 = Phosphate) (331-271)

(SEQ ID NO: 14)
5TAYGAYGARATHAAYGA  (R = A, G; Y = T, C; H = A, T,

C; 5 = Phosphate; 5 = Phosphate) (331-272)
```

The inverse PCR consisted of: 10 µl of each primers (270 or 271, 272), 10 µl ThermoPol reaction buffer, 10 µl DNA templates as prepared above, 4 µl dNTP, 2 µl $MgSO_4$, 52 µl $H_2O$ and 2 µl of Taq DNA polymerase (NEB, Ipswich, Mass.). The PCR procedure consisted of one cycle of 95° C., 35 cycles of 95° C. for 30 sec, 37° C. to 55.5° C. for 30 sec with 0.5° C. increase for every cycle, 72° C. 2 min, and a final extension of 2 min at 72° C.

The primer pair of 331-271 and 331-272 with different templates produced multiple DNA bands. A total of 26 DNA fragments were purified from low-melting gels and sequenced by primers 331-271 and 331-272.

6. The Designation of Gene NruIR

After DNA sequencing, the DNA fragments #3, #16, #17 and #26 generated a 774-bp contig. When the DNA sequence was translated into amino acid sequence, it shows 55% similarity and 46% identity to Sbo13I endonuclease protein sequence (FIG. 1). DNA restriction endonucleases are quite different from each other if they are not isoschizomers. So this high degree of amino acid sequence similarity immediately identified this contig to be the gene fragment encoding NruI restriction endonuclease. The other 17 DNA contigs were presumably amplified from genomic DNA non-specifically.

The remaining of the NruI R-M system was revealed by subsequent inverse PCR. The NruI R-M system consisted of R and M genes running in the opposite direction, with 350 bps at both side (FIG. 2). The nruIM gene is 804 bp and encodes a polypeptide of 267 amino acids (FIGS. 3A-1 and #3A-2), and the nruIR gene is 660 bp and encodes a polypeptide of 219 amino acids (FIGS. 3B-1 and 3B-2). The N-terminal of the translated nruIR is MGFLEDWDLSYDEINELTDN (SEQ ID NO:15), which closely matches the N-terminal sequence derived from the native NruI (MGFLADXDLSY-DEINELLTDN) (SEQ ID NO:11). Another important discovery was that when the amino acid sequence of nruIM was compared to other known methylases in GenBank by Blastx, the nruIM gene did not match any methylase sequence other than the sbo13IM gene. M.NruI and M.Sbo13I share a unique amino acid sequence among the DNA methylases. Such an amino acid sequence was not found in other N4C or N6A methylases.

7. Establishment of Pre-Modified E. Coli Strain for Expression of NruI Restriction Endonuclease The non-cognate methylase gene sbo13IM was amplified in PCR and cloned into pACYC184 by the following primers:

```
                                        (SEQ ID NO: 16)
5'-GGTGGTGGATCCGGAGGTAAATAAATGGTGATTTTAGCAGATATTAA

AATAGAC-3'

(SEQ ID NO: 17)
5'-GGTGGTGTCGACTCATAACGTTTTCTTCTTTCTTTTCTTTTC-3'
```

The PCR was performed under the following conditions: 10 μl Shigella boydii 13 genomic DNA, 80 pmol primers, 400 μM dNTPs, 4 units of Deep Vent DNA polymerase (NEB, Ipswich, Mass.) in 1× ThermoPol buffer (NEB, Ipswich, Mass.). The reaction condition was carried out at 94° C. for 5 min in one cycle followed by 30 cycles of 94° C. 30 sec, 55° C. 30 sec and 72° C. 48 sec. The PCR product was then digested with BamHI and SalI, and ligated into pACYC184 with compatible ends. The ligated plasmid was transformed into ER2683 and plated on LB agar plate with Cm. Ten colonies were grown and plasmid DNA was isolated. The plasmids were digested with NruI to check the resistance against NruI. All ten isolates were found to be resistant. Plasmid pACYC-sbo13IM was transferred into ER2683 to generate a pre-modified strain.

8. Over-Expression of NruI in E. Coli

The nruIR gene was amplified in PCR using the following two primers.

```
                                        (SEQ ID NO: 18)
5'-GGTGGTCTGCAGGGAGGTAAATAAATGGGATTTCTTGAAGACTGGGA

C-3'

(SEQ ID NO: 19)
5'-GGTGGTGGTACCTCACTCTTCGTCTTCGATGATCTT-3'
```

Figure 6:
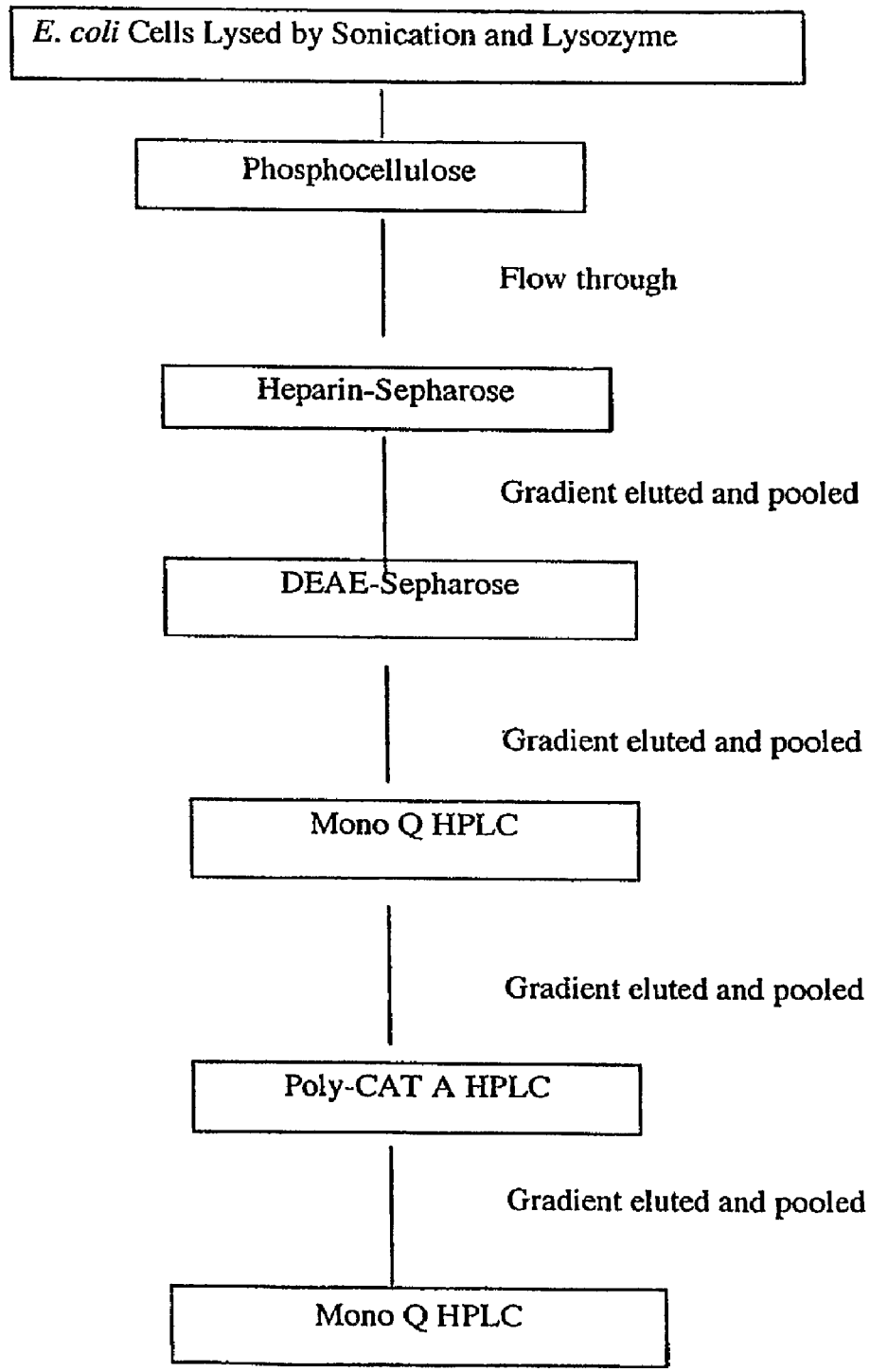
FIG. 6 illustrates the scheme for producing the Sbo13I restriction endonuclease.
Figure 7:
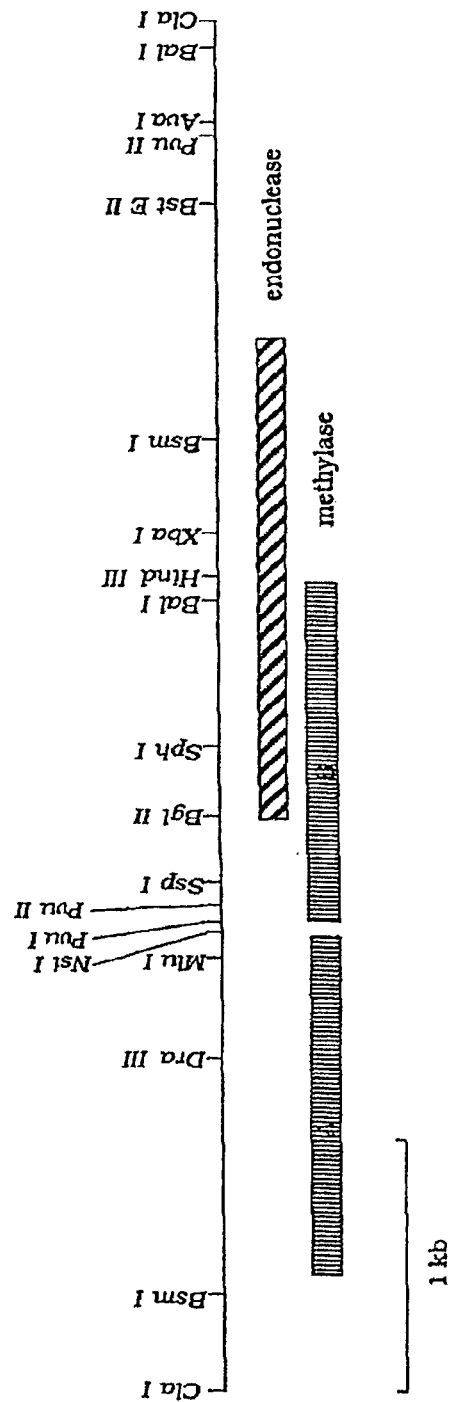
FIG. 7 is a photograph of an agarose gel demonstrating Sbo13I restriction endonuclease activity in cell extracts of *E. coli* RR1 (ATCC 31343) carrying pBLSboC13RM8.1-A1, pBLSboC13RM9.6-A8, pBLSboC13RM9.6-A2 and pBLSboC13RM9.6-B6.

PCR condition was as following: 10 μl Norcardia rubra genomic DNA, 80 pmol primers, 400 μM dNTP, 4 units of Deep Vent DNA polymerase (NEB, Ipswich, Mass.) in 1× ThermoPol buffer (NEB, Ipswich, Mass.). The reaction condition was 94° C. for 5 min, 1 cycle; 95° C. for 30 sec, 55° C. for 30 sec, 72° C. for 46 sec for 30 cycles. The PCR product was digested by PstI and Acc65I and ligated to pUC19 digested with same pair of enzymes. The ligated plasmid was transformed into ER2683 [pACYC-sbo13IM] Transformants were plated on LB agar supplemented with Amp and Cam. Colonies were picked and grown in 4 ml LB with Amp and Cam overnight. Ten μl overnight cell culture from 38 samples was tested for NruI activity on lambda DNA, 37° C., 30 min in NEB buffer 2 (Ipswich, Mass.). Eight out of 24 (#7, #10, #14, #15, #16, #18, #19, #20) can digest lambda DNA into complete pattern. The inserts in three clones (#10, #14, #15) were sequenced using the universal primers from pUC19 vector (S1233S and S1224S). All inserts were confirmed to carry the wild-type nruIR sequence. #14 was selected and deposited as a production strain. The strain was then subjected to a stability test in a large culture by passing 10 ml of cells from 1 L overnight culture to a fresh 1 L culture. The NruI expression strain was grown in 25 L culture in constitutive expression. After overnight culture, the final expression level of NruI was found to be ~$6.5 \times 10^6$ units per gram of wet cells (FIG. 6). In comparison, the native Norcardia rubra cells produces approximately $10^4$ units NruI per gram of wet cells. The recombinant over-expression clone produced 600-fold more NruI than the native strain.

Example 2

Cloning of Sbo13I Restriction Endonuclease Gene

To prepare the plasmid DNA of Shigella boydii C13, 3 grams of cell paste was resuspended in 14 ml of 25 mM Tris-HC1, 10 mM EDTA pH 8.0 and 50 mM glucose. The suspension was made 1.0 mg/ml in lysozyme and incubated at 25° C. for 5 minutes. A 27 ml aliquot of 1% sodium dodecyl sulfate and 0.2 N NaOH was added followed by mixing of the solution and incubated for 5 minutes on ice. Genomic DNA was precipitated by the addition of 20 ml of ice-cold 3M potassium acetate, pH 4.8, vortexed gently for 10 seconds, left on ice for 5 minutes and centrifuged at 12,000×g for ten minutes. The supernatant was removed and extracted with an equal volume of phenol/chloroform (1:1). The layers were separated by centrifugation at 10,000×g for 5 minutes. The upper layer was removed and the nucleic acids precipitated by the addition of two volumes of ethanol. The precipitate was collected by centrifugation at 12,000×g for ten minutes. The pellet was washed with 70% ethanol once and repelleted as before. The pellet was dried under vacuum and resuspended in 8 ml of 10 mM Tris-HC1, 1 mM EDTA, pH 8.0 containing 20 μg/ml of RNAse. The DNA solution was incubated at 37° C. for one hour and then prepared for cesium chloride-ethidium bromide equilibrium density centrifugation by the addition of 8.8 grams of cesium chloride and 0.4 ml of a solution of ethidium bromide (5 mg/ml) were added. The DNA solution was centrifuged at 44,000 rpm for 48 hours and the resulting plasmid band of DNA was removed by extracting with an equal volume of CsCl-water-saturated isopropanol. The cesium chloride was removed by dialysis. The DNA was extracted with an equal volume of phenol/chloroform (1:1), extracted with an equal volume of chloroform, and subjected to dialysis.

The Sbo13I restriction system containing plasmid was enriched by establishment in E. coli strain RR1 by simultaneous co-transformation with the vectors pBR322 and pACYC184. One μg of Sbo13I plasmid DNA (as prepared above) was added to tubes containing 0.1 µg of pBR322 or pACYC184 DNA and 200 µl of ice-cold competent *E. coli* RR1 cells and placed on ice for thirty minutes. After a 2-minute heat shock at 43° C., the cells were diluted into one ml of Luria-broth (L-broth) and grown for one hour at 37° C. The transformed cell cultures were centrifuged, resuspended in 250 µl volumes and plated onto Luria-agar (L-agar) plates containing 100 µg/ml ampicillin (pBR322) or 25 µg/ml tetracycline (pACYC184). After overnight incubation at 37° C., the plates were removed and 48 colonies from each co-transformation were picked into 200 µl of LB with antibiotic in microtiter well plates. Master plates were prepared by stamping on LB with antibiotic. Replica plates were prepared by stamping onto four levels of T4 and T7 phage: 109, 107, 105, and 103 phage/plate. Individual colonies, which survived on all the levels of phage were considered positive and phage-resistant. Eleven colonies from the ampicillin-selected pBR322 co-transformation and five colonies from the tetracycline-selected pACYC 184 co-transformation of RR1 were found to be phage-resistant. Colonies from the positively screened phage-resistant colonies from each co-transformation were grown up into 10 ml cultures and the plasmids that they carried were prepared by the following miniprep purification procedure, adapted from the method of Birnboim and Doly (*Nucleic Acids Res.* 7:1513 (1979)).

Each culture was processed as follows: The 1.5 ml overnight culture was pelleted at 6,000×g for 2 minutes. The supernatant was poured off and the cell pellet was resuspended in 150 µl of 25 mM Tris, 10 mM EDTA, 50 mM glucose, pH 8.0, containing 1 mg/ml lysozyme. After five minutes at room temperature, 200 µl of 0.2M NaOH, 1% SDS was added and the tube was shaken to lyse the cells then placed on ice. After five minutes, 150 µl of 3M sodium acetate, pH 4.8, was added and shaken and placed on ice for an additional five minutes. The precipitate that formed was spun down at 12,000×g, 4° C. for 10 minutes. The supernatant was removed and extracted with an equal volume of phenol/chloroform (1:1). The layers were separated by centrifugation at 10,000×g for five minutes. The supernatant was poured into a centrifuge tube containing 880 µl of ethanol and mixed. After 10 minutes at room temperature, the tube was spun at 12,000×g for 10 minutes to pellet the precipitated nucleic acids. The supernatant was discarded and the pellet was washed again with one ml of 70% ethanol-water, repelleted and dried at room temperature for 30 minutes under vacuum. Once dry, the pellet was resuspended in 50 µl of 10 mM Tris, 1 mM EDTA, pH 8.0 containing 20 ug/ml Rnase and incubated for 1 hour at 37° C. to digest the RNA.

The remaining portion of the overnight culture was used to check for endonuclease activity. This was done as described below.

Endonuclease assays were performed as follows:

A 10× restriction endonuclease buffer 100 mM Tris, pH 7.5, 100 mM MgC12, 100 mM 2-mercaptoethanol, 550 mM NaCl was used for the assays.

Cell extracts were prepared as follows: Cells from one ml were pelleted by centrifugation at 4,000 rpm for five minutes. The supernatant was discarded and the pellet was resuspended in one ml of sonication buffer (10 mM Tris, pH 7.5, 100 mM NaCl, 10 mM mercaptoethanol, 1 mM EDTA) containing one mg/ml lysozyme. The suspension was swirled and left on ice for thirty minutes. A one ml ample was transferred to an Eppendorf tube and sonicated gently for two 10-second bursts to disrupt the cells. The tube was spun for five minutes in a microfuge and the supernatant was used as the cell extract. The extract, 1 µl and 5 µl, were incubated with one µg of lambda DNA in 50 µl of 1× restriction endonuclease buffer for five minutes at 37° C. All these colonies were found to stably carry the Sbo13I restriction system. One isolate from the ampicillin selected pBR322 co-transformation was selected for further characterization. This isolate was designated A5.

The A5 isolate was used to map the 5.4 kb restriction system-containing plasmid for single sites. Ten µl aliquots of the A5 isolate were subjected to digestion with five to ten units of more than forty enzymes in 25 µl of 10 mM Tris pH 7.5, 10 mM MgC12, 50 mM NaC1, 10 mM mercaptoethanol buffer and found to contain single sites for the following enzymes: AvaI, BalI, Bg II, BsmI, BstEII, ClaI, DraIII, HindIII, MluI, NsI, PvuI, SphI, SspI and XbaI.

The purified A5 isolate DNA was cut with ClaI, HindIII and NsiI to achieve total digestion as follows: 50 ul of DNA at 100 µg/ml in 10 mM Tris pH 7.5, 10 mM MgC12, 50 mM NaC1, 10 mM mercaptoethanol buffer was dispensed into three tubes. To each tube was added 10 units of ClaI, HindIII or NsiI. The tubes were incubated at 37° C. for one hour, then phenol/chloroform extracted and ethanol precipitated. The pellets were redissolved in 100 µl of 10 mM Tris-HC1, 1 mM EDTA, pH 8.0 and 10 µl from each analyzed by agarose gel electrophoresis.

The fragmented DNA was ligated to pUC19 or pBR322 as follows: 1.0 µl of ClaI-digested *Shigella boydii* C13 plasmid DNA (15 µl) was mixed with 0.2 µg of ClaI-cleaved and dephosphorylated pBR322 (2.5 µl) or with 0.2 µg of AccI-cleaved and dephosphorylated pUC19 (2.5 µl). 2.5 µl of 10× ligation mix (500 mM Tris, pH7.5, 100 mM MgCl$_2$, 100 mM DTT, 5 mM ATP) was added plus 2.5 µl of sterile distilled water to bring the final volume to 25 µl. 1.0 µl of T4 DNA ligase was added and the mixture allowed to incubate at 16° C. for 16 hours. Aliquots of 2.5 and 5.0 µl were used to transform *E. coli* strain RR1 as follows: Each aliquot was mixed with 200 µl of ice-cold competent *E. Coli* RR1 cells and placed on ice for thirty minutes. After a 2-minute heat shock at 42° C., the cells were diluted with one ml of Luria-broth (L-broth) and grown for one hour at 37° C.

The transformed cell cultures were centrifuged, resuspended in 250 µl volumes and plated onto Luria-agar (L-agar) plates containing 100 µg/ml ampicillin in 25 µg/ml tetracycline. After overnight incubation at 37° C., the plates were removed and colonies picked into 200 µl of LB with antibiotic into microtiter well plates. Master plates were prepared by stamping on LB with antibiotic. Replica plates were prepared by stamping onto four levels of T4 and T7 phage: 109, 107, 105, and 103 phage/plate. Individual colonies that survived on all the levels of phage were considered positive and phage-resistant.

Approximately 18 of the positively screened phage-resistant colonies from each ligation were grown up into 10 ml cultures and the plasmids that they carried were prepared by the previously described miniprep purification procedure. The plasmid minipreps were subsequently analyzed by digestion with Sbo13I.

Many of the plasmids that were analyzed were found to carry random ClaI or NsiI fragments of DNA to be sensitive to digestion of Sbo13I. These plasmids were spurious survivors of no further interest. The remaining plasmids, however, were found to be both resistant to Sbo13I and to carry ClaI or NsiI fragments of approximately 5.4 kb in length. These plasmids were subsequently shown to carry both the Sbo13I modification methylase and restriction endonuclease genes.

The clones identified above with the Sbo13I modification methylase gene were also tested for the Sbo13I restriction endonuclease gene. This was performed as described before. All methylase positive clones except those from the HindIII ligation were found to contain endonuclease. These clones were found to synthesize about 100,000 units of Sbo13I restriction endonuclease per gram of wet cell paste.

The recombinant plasmid pBLSboC13M8.1 that carries the gene encoding the Sbo13I restriction endonuclease and methylase was transferred to *E. coli* strain RR1 by transformation.

Production of Sbo13I endonuclease from *E. coli* host cells was performed as follows: *E. coli* RR1/pBLSboC13M8.1-AI designated NEB #445 was propagated in a fermenter at 37° C. in L Broth medium consisting of: 10 grams per liter, casein hydrolysate; 5 grams per liter, yeast extract; 10 grams per liter, NaC1; 1 gram per liter, magnesium chloride-hexahydrate; 1 gram per liter, glucose; 100 mg per liter, ampicillin. The pH is adjusted to 7.2 with NaOH. The cells were collected by centrifugation and the cell paste was used fresh or stored at −70° C. All subsequent steps were carried out at 4° C.

The cell paste (24 grams) was thawed and the cells were resuspended in 100 mls sonication buffer (25 mM Tris-HC1, pH 8.0, 100 mM NaCl, 10 mM β-mercaptoethanol and 10 mM EDTA).

The cells were disrupted by sonication (250 watts for two minutes, cooled on ice for five minutes, three times), to achieve release of approximately 50 mg of soluble protein per ml of suspended cells.

The insoluble cell debris was removed by centrifugation at 21,000×g for 20 minutes.

The supernatant fluid applied to phosphocellulose column (5×35 cm) (Whatman P-11) was equilibrated with 20 mM KH2PO4, pH 6.9, 100 mM NaCl, and 10 mM β-mercaptoethanol. The column was washed with two column volumes of the above buffer. The flow-through from the column was collected in a single flask. No Sbo13I endonuclease was retained by the column.

The flow-through from the phosphocellulose column was applied to a Heparin-Sepharose CL-6B column (2.5×25 cm) equilibrated with 20 mM Tris-HC1, pH 7.4, 50 mM NaCl, from 0.1 M to 1.0 M (total volume 700 ml) and developed and applied to the column. Then 10 ml fractions were collected. The fractions were assayed for the presence of the Sbo13I restriction endonuclease activity on lambda DNA. The active fractions were pooled and dialysed against 100 volumes of buffer (50 mM KC1; 20 mM Tris-HCL, ph 7.4; 10 mM β-mercaptoethanol).

The dialyzed pool (50 ml) of Sbo13I activity was applied to a DEAE-Sepharose CL-6B column (2.5 cm×25 cm) equilibrated with 20 mM Tris-HC1, pH 7.4, 50 mM KC1, and 10 mM 2-mercaptoethanol and washed with two column volumes of buffer containing 0.1 M KCl. A linear gradient of KCl from 0.1M to 1.0M (total volume 400 ml) was developed and applied to the column. Ten ml fractions were collected. The fractions were assayed for the presence of the Sbo13I restriction endonuclease activity on lambda DNA. The active fractions were pooled and dialysed against 100 volumes of buffer (50 mM KCl; 20 mM Tris-HC1; pH 7.4; 10 mM β-mercaptoethanol).

The dialysate was applied to a 1 ml Mono-Q FPLC column (Pharmacia, Piscataway, N.J.) and washed with buffer Q (0.020M Tris-HC1, pH 7.4; 50 mM KCl; 10 mM β-mercaptoethanol) and a 40 ml linear gradient from 50 mM KCl to 0.6 M KC1 is developed in Q buffer and applied to the column. One ml fractions were collected and assayed for the presence of Sbo13I restriction endonuclease activity. The two most active fractions were pooled.

The above pool was diluted ten-fold with 50 mM KCl in buffer C (20 mM KH2PO4, pH 6.9, 50 mM NaCl, and 10 mM β-mercaptoethanol) and was applied to a Poly-CAT-A 10 μm particle size, 4.6×100 mm HPLC column (Custom LC) and washed with C buffer. A 40 ml linear gradient from 50 mM KCl to 0.6 M KCl was developed in C buffer and applied to the column. One ml fractions were collected and assayed for the presence of Sbo13I restriction endonuclease activity. The four most active fractions were pooled.

The dialysate was reapplied to a 1 ml Mono-Q FPLC column and eluted as before from this column to concentrate the endonuclease. One ml fractions were collected and assayed for the presence of Sbo13I restriction endonuclease activity. The two most active fractions were homogeneous.

What is claimed is:

1. An isolated DNA encoding a restriction endonuclease comprising an amino acid sequence having at least 90% sequence identity with SEQ ID NO:2, wherein the restriction endonuclease binds to a symmetric nucleotide sequence 5'-TCGCGA-3' in double stranded DNA molecules and cleaves the DNA molecules in the center of the symmetric nucleotide sequence, thereby producing DNA fragments with blunt ends.

2. A vector comprising a DNA encoding a restriction endonuclease comprising an amino acid sequence having at least 90% sequence identity with SEQ ID NO:2, wherein the restriction endonuclease binds to a symmetric nucleotide sequence 5'-TCGCGA-3' in double stranded DNA molecules and cleaves the DNA molecules in the center of the symmetric nucleotide sequence, thereby producing DNA fragments with blunt ends.

3. An isolated host cell comprising a recombinant DNA encoding a restriction endonuclease comprising an amino acid sequence having at least 90% sequence identity with SEQ ID NO:2, wherein the restriction endonuclease binds to a symmetric nucleotide sequence 5'-TCGCGA-3' in double stranded DNA molecules and cleaves the DNA molecules in the center of the symmetric nucleotide sequence, thereby producing DNA fragments with blunt ends.

4. The host cell according to claim 3, wherein the chromosomal DNA in said host cell has been methylated.

5. The host cell according to claim 4, wherein the chromosomal DNA has been methylated with a non-cognate methylase.

6. A method of producing a recombinant restriction endonuclease, comprising: culturing a host cell transformed with the vector of claim 2 under conditions suitable for expression of the restriction endonuclease.

7. The isolated DNA of claim 1, wherein the DNA encodes a restriction endonuclease comprising the amino acid sequence of SEQ ID NO:2.

8. The host cell according to claim 4, wherein the chromosomal DNA has been methylated with the methylase or the NruI methylase.

9. The isolated DNA of claim 1, wherein the DNA comprises the nucleotide sequence of SEQ ID NO:1.

* * * * *

UNITED STATES PATENT AND TRADEMARK OFFICE
CERTIFICATE OF CORRECTION

PATENT NO. : 8,361,773 B2
APPLICATION NO. : 12/297097
DATED : January 29, 2013
INVENTOR(S) : Zhenyu Zhu et al.

It is certified that error appears in the above-identified patent and that said Letters Patent is hereby corrected as shown below:

In the Claims:

Column 28, claim number 8, line number 48, replace "DNA has been methylated with the methylase or the NruI methylase" with
"DNA has been methylated with the Sbo13I methylase or the NruI methylase."

Signed and Sealed this
Thirtieth Day of July, 2013

Teresa Stanek Rea
*Acting Director of the United States Patent and Trademark Office*

SEQUENCE LISTING

```
<160> NUMBER OF SEQ ID NOS: 19

<210> SEQ ID NO 1
<211> LENGTH: 660
<212> TYPE: DNA
<213> ORGANISM: unknown
<220> FEATURE:
<223> OTHER INFORMATION: NruI restriction endonuclease gene

<400> SEQUENCE: 1
atgggatttc ttgaagactg ggacctcagc tacgacgaga tcaacgagct tctcactgac      60
aaccccagcc ttcgatcgtt cgtgatgggg tacgcagcgg agatcaagtg tcgcaacatg     120
ttcttcgttg atcatccaca tatcaccaac atttacaagc ccgatgatca cgatcgcact     180
gaaaagggcg actggatcat caactacaag ggacaccgga tcggggtcga ggtcaagagt     240
ctccagacga actcactgcg gcttcgccga gatggcagtg tccgaccaaa ctaccagtgc     300
gacgcttcgg atgcccgcac cgtgatcttc gctgacggta gcgaagttca tacgaccgct     360
ctgttggtcg gagaatttga cgtagttgca gtcaatatcc atgcgttcga aaataagtgg     420
gattttgcgt tcgctaagaa cgaggatctc atcacgatgg agggtgcgac caggggcgca     480
```

```
gcgaaagact acaccgaact ccagaaacgc aatctcatca agactctcca accgatgcct    540
atggacgtgc cagccccgta cactcgagat cccttcaaac tcttcgacga gatcatcgaa    600
gagcgcatga agggtgagca gcctcagctc aaggcgaaga tcatcgaaga cgaagagtga    660
```

<210> SEQ ID NO 2
<211> LENGTH: 219
<212> TYPE: PRT
<213> ORGANISM: unknown
<220> FEATURE:
<223> OTHER INFORMATION: encoded amino acid seqence of NruI restriction
      endonuclease gene

<400> SEQUENCE: 2

```
Met Gly Phe Leu Glu Asp Trp Asp Leu Ser Tyr Asp Glu Ile Asn Glu
1               5                   10                  15

Leu Leu Thr Asp Asn Pro Ser Leu Arg Ser Phe Val Met Gly Tyr Ala
            20                  25                  30

Ala Glu Ile Lys Cys Arg Asn Met Phe Phe Val Asp His Pro His Ile
        35                  40                  45

Thr Asn Ile Tyr Lys Pro Asp Asp His Asp Arg Thr Glu Lys Gly Asp
    50                  55                  60

Trp Ile Ile Asn Tyr Lys Gly His Arg Ile Gly Val Glu Val Lys Ser
65                  70                  75                  80

Leu Gln Thr Asn Ser Leu Arg Leu Arg Arg Asp Gly Ser Val Arg Pro
                85                  90                  95

Asn Tyr Gln Cys Asp Ala Ser Asp Ala Arg Thr Val Ile Phe Ala Asp
            100                 105                 110

Gly Ser Glu Val His Thr Thr Ala Leu Leu Val Gly Glu Phe Asp Val
        115                 120                 125

Val Ala Val Asn Ile His Ala Phe Glu Asn Lys Trp Asp Phe Ala Phe
    130                 135                 140

Ala Lys Asn Glu Asp Leu Ile Thr Met Glu Gly Ala Thr Arg Gly Ala
145                 150                 155                 160

Ala Lys Asp Tyr Thr Glu Leu Gln Lys Arg Asn Leu Ile Lys Thr Leu
                165                 170                 175

Gln Pro Met Pro Met Asp Val Pro Ala Pro Tyr Thr Arg Asp Pro Phe
            180                 185                 190

Lys Leu Phe Asp Glu Ile Ile Glu Glu Arg Met Lys Gly Glu Gln Pro
        195                 200                 205

Gln Leu Lys Ala Lys Ile Ile Glu Asp Glu Glu
    210                 215
```

<210> SEQ ID NO 3
<211> LENGTH: 137
<212> TYPE: PRT
<213> ORGANISM: unknown
<220> FEATURE:
<223> OTHER INFORMATION: inverse PCR product (NruII)

<400> SEQUENCE: 3

```
Leu Glu Asp Trp Asp Leu Ser Tyr Asp Glu Ile Asn Glu Leu Leu Thr
1               5                   10                  15

Asp Asn Pro Ser Leu Arg Ser Phe Val Met Gly Tyr Ala Ala Glu Ile
            20                  25                  30

Lys Cys Arg Asn Met Phe Phe Val Asp His Pro His Ile Thr Asn Ile
        35                  40                  45

Tyr Lys Pro Asp Asp His Asp Arg Thr Glu Lys Gly Asp Trp Ile Ile
    50                  55                  60
```

```
Asn Tyr Lys Gly His Arg Ile Gly Val Glu Val Lys Ser Leu Gln Thr
 65                  70                  75                  80

Asn Ser Leu Arg Leu Arg Arg Asp Gly Ser Val Arg Pro Asn Tyr Gln
             85                  90                  95

Cys Asp Ala Ser Asp Ala Arg Thr Val Ile Phe Ala Asp Gly Ser Glu
            100                 105                 110

Val His Thr Thr Ala Leu Leu Val Gly Glu Phe Asp Val Val Ala Val
        115                 120                 125

Asn Ile His Ala Phe Glu Asn Lys Trp
    130                 135

<210> SEQ ID NO 4
<211> LENGTH: 136
<212> TYPE: PRT
<213> ORGANISM: unknown
<220> FEATURE:
<223> OTHER INFORMATION: Sbo13I restriction endonuclease

<400> SEQUENCE: 4

Leu Glu Arg Trp Glu Ile Ser Glu Glu Lys Leu Thr Asp Leu Val Asp
  1               5                  10                  15

Lys Asn Pro Ser Leu Arg Gly Met Ile Leu Gly Tyr Val Ala Glu Asp
             20                  25                  30

Lys Phe His Glu Leu Phe Leu Glu Asp Glu Arg Val Lys Glu Val Ser
             35                  40                  45

Lys Asp Asp His Asp Arg Lys Lys Gly Asp Arg Thr Phe Ile
         50                  55                  60

Tyr Lys Gly Lys Lys Phe Thr Val Glu Val Lys Ser Leu Gln Thr Ala
 65                  70                  75                  80

Met Cys Lys Lys Asn Glu Asp Gly Thr Tyr Ser Gly Lys Ala Gln Val
             85                  90                  95

Asp Gly Ser Asp Arg Arg Ile Val Lys Phe Pro Asp Asn Ser Glu Leu
            100                 105                 110

Asn Thr Thr Leu Leu Leu Lys Gly Glu Phe Asp Leu Leu Ala Val Asn
        115                 120                 125

Cys Phe Ala Phe Gly Glu Gly Trp
    130                 135

<210> SEQ ID NO 5
<211> LENGTH: 804
<212> TYPE: DNA
<213> ORGANISM: unknown
<220> FEATURE:
<223> OTHER INFORMATION: NruI methylase gene

<400> SEQUENCE: 5
gtgactgagc ccaagcgacg tgttgccaaa ggtgtctcta caacggatgt tgtccttagc      60
tcatccgtcg gtgacaatgc cccggtcttc gtggacatcc tccggctttt cgtacccgtc     120
gggtcgacga ttgctgatgt cacgtggggc aagggcgctt tttggcgagc ggtaccggag     180
ggtctataca aggtactcgc cacggacatt cagatgggga tggattgcag agacctcccg     240
tatgacgacg gctccgtcga tgcactcgtg ctcgaccctc cctacatgga gggattgttc     300
cgtaaagagt catcccacat ggcgggtggc gggagccacg gagcattccg agagcgctat     360
agcaactccg cggcgactcc tgaggtcgaa ggagctccga agtatacgga tgctgttctt     420
gatctttacc tgaaggctgg tgaagaagct aagcgcgtcc tccgcaacta cggcgtgttt     480
attgtgaagt gccaggatga ggtgtcggcc aaccgtcaaa ggttgaccca tatcgaactc     540
```

```
tacaacgcct gggagaagga cttctattgt aaggatcttt tcgtagttac cagagccaac    600
cggccgggag tgtcccgcct actaaagcaa gagcatgctc gtaaaaatca cagttacttt    660 atgatttta tcaagcggaa ccccgaatat cccaagagga ttcggccgac cgcaaaggag    720
gctaagcttc tgggcctcga caacccgaag ccgtggccgt cctcagtgct gctgacggaa    780
ggtgacgggg atagtctttt ctag                                          804
```

```
<210> SEQ ID NO 6
<211> LENGTH: 267
<212> TYPE: PRT
<213> ORGANISM: unknown
<220> FEATURE:
<223> OTHER INFORMATION: NruI methylase encoded amino acid sequence

<400> SEQUENCE: 6
```

Met Thr Glu Pro Lys Arg Arg Val Ala Lys Gly Val Ser Thr Thr Asp
1               5                   10                  15

Val Val Leu Ser Ser Val Gly Asp Asn Ala Pro Val Phe Val Asp
            20                  25                  30

Ile Leu Arg Leu Phe Val Pro Val Gly Ser Thr Ile Ala Asp Val Thr
        35                  40                  45

Trp Gly Lys Gly Ala Phe Trp Arg Ala Val Pro Glu Gly Leu Tyr Lys
    50                  55                  60

Val Leu Ala Thr Asp Ile Gln Met Gly Val Asp Cys Arg Asp Leu Pro
65                  70                  75                  80

Tyr Asp Asp Gly Ser Val Asp Ala Leu Val Leu Asp Pro Pro Tyr Met
                85                  90                  95

Glu Gly Leu Phe Arg Lys Glu Ser Ser His Met Ala Gly Gly Ser
            100                 105                 110

His Gly Ala Phe Arg Glu Arg Tyr Ser Asn Ser Ala Ala Thr Pro Glu
        115                 120                 125

Val Glu Gly Ala Pro Lys Tyr His Asp Ala Val Leu Asp Leu Tyr Leu
    130                 135                 140

Lys Ala Gly Glu Glu Ala Lys Arg Val Leu Arg Asn Tyr Gly Val Phe
145                 150                 155                 160

Ile Val Lys Cys Gln Asp Glu Val Ser Ala Asn Arg Gln Arg Leu Thr
                165                 170                 175

His Ile Glu Leu Tyr Asn Ala Trp Glu Lys Asp Phe Tyr Cys Lys Asp
            180                 185                 190

Leu Phe Val Val Thr Arg Ala Asn Arg Pro Gly Val Ser Arg Leu Leu
        195                 200                 205

Lys Gln Glu His Ala Arg Lys Asn His Ser Tyr Phe Met Ile Phe Ile
    210                 215                 220

Lys Arg Asn Pro Glu Tyr Pro Lys Arg Ile Arg Pro Thr Ala Lys Glu
225                 230                 235                 240

Ala Lys Leu Leu Gly Leu Asp Asn Pro Lys Pro Trp Pro Ser Ser Val
                245                 250                 255

Leu Leu Thr Glu Gly Asp Gly Asp Ser Leu Phe
            260                 265

```
<210> SEQ ID NO 7
<211> LENGTH: 762
<212> TYPE: DNA
<213> ORGANISM: unknown
<220> FEATURE:
<223> OTHER INFORMATION: Sbo13I methylase gene
```

-continued

<400> SEQUENCE: 7

```
atggtgattt tagcagatat taaaatagac gacgtagaag cggaacacac tgaaattaaa        60
aagaaaaaga gagttcaagg tggtgaggct acgagtaatg taacaatgtc agcacacctg       120
agcggcaacg ccgaagtttt cccgcaaatc ctagacttgc atgttcctga aggggctgtg       180
attgcggatg tcacttttgg tggcggcgta ttttggaaaa aagttaatct tgataagtac       240
aagctgttgg caacagatat tgctaacgga gtcgattgtc gagatctccc ttatgaggaa       300
acaagccttg atgccttagt acttgatcct ccatatatgg agggattact tcgcaacaat       360
gcttcgcaca agcagggga tggaacacat tctacgttca ggaaatatta ctctaacggc       420
gacgaaaaaa gtgtagcggg ggctccaaaa tggcatgcgg ctgttaccga tctttattat       480
aaagctagtg atgaagcatt tagggtttta aaagataatg gtgttttat tgtaaaatgc       540
caagatgagg tttcggctaa caaacaatgg ttgactcatg ttgaaataat aaactattgc       600
gaatctcttg gcttctatac taaagatctt tttgtcgttg ttcgtagtaa caaggctggg       660
gtttctcgaa tgaagaagca ggttcatgca aggaagaatc acagttactt ccttgttttt       720
ataaaacttc cggaaaagaa aagaaagaag aaaacgttat ga                          762
```

<210> SEQ ID NO 8
<211> LENGTH: 253
<212> TYPE: PRT
<213> ORGANISM: unknown
<220> FEATURE:
<223> OTHER INFORMATION: Sbo13I methylase encoded amino acid sequence

<400> SEQUENCE: 8

```
Met Val Ile Leu Ala Asp Ile Lys Ile Asp Asp Val Glu Ala Glu His
 1               5                  10                  15

Thr Glu Ile Lys Lys Lys Arg Val Gln Gly Gly Glu Ala Thr Ser
             20                  25                  30

Asn Val Thr Met Ser Ala His Leu Ser Gly Asn Ala Glu Val Phe Pro
         35                  40                  45

Gln Ile Leu Asp Leu His Val Pro Glu Gly Ala Val Ile Ala Asp Val
     50                  55                  60

Thr Phe Gly Gly Gly Val Phe Trp Lys Lys Val Asn Leu Asp Lys Tyr
 65                  70                  75                  80

Lys Leu Leu Ala Thr Asp Ile Ala Asn Gly Val Asp Cys Arg Asp Leu
                 85                  90                  95

Pro Tyr Glu Glu Thr Ser Leu Asp Ala Leu Val Leu Asp Pro Pro Tyr
            100                 105                 110

Met Glu Gly Leu Leu Arg Asn Asn Ala Ser His Lys Ala Gly Asp Gly
        115                 120                 125

Thr His Ser Thr Phe Arg Lys Tyr Tyr Ser Asn Gly Asp Glu Lys Ser
    130                 135                 140

Val Ala Gly Ala Pro Lys Trp His Ala Ala Val Thr Asp Leu Tyr Tyr
145                 150                 155                 160

Lys Ala Ser Asp Glu Ala Phe Arg Val Leu Lys Asp Asn Gly Val Phe
                165                 170                 175

Ile Val Lys Cys Gln Asp Glu Val Ser Ala Asn Lys Gln Trp Leu Thr
            180                 185                 190

His Val Glu Ile Ile Asn Tyr Cys Glu Ser Leu Gly Phe Tyr Thr Lys
        195                 200                 205

Asp Leu Phe Val Val Val Arg Ser Asn Lys Ala Gly Val Ser Arg Met
    210                 215                 220
```

```
Lys Lys Gln Val His Ala Arg Lys Asn His Ser Tyr Phe Leu Val Phe
225                 230                 235                 240

Ile Lys Leu Pro Glu Lys Lys Arg Lys Lys Thr Leu
                245                 250
```

<210> SEQ ID NO 9
<211> LENGTH: 675
<212> TYPE: DNA
<213> ORGANISM: unknown
<220> FEATURE:
<223> OTHER INFORMATION: DNA sequence of Sbo13I restriction endonuclease gene

<400> SEQUENCE: 9

```
atgagagaac cctcgattct agaaagatgg gaaataagcg aagaaaaatt aactgacttg      60
gttgataaaa acccctctct tagaggaatg attttaggtt atgttgctga ggataaattt     120
cacgagctat tccttgaaga tgaaagagta aaggaggttt ctaaagacga cgatcatgac     180
agaaagaaaa aaggagatag aacctttatt tacaaaggta aaaaatttac agttgaagtt     240
aaaagcttgc aaaccgcaat gtgcaagaaa aatgaagacg gaacttattc aggaaaagcc     300
caagtagacg gcagtgatcg aagaatagta aaattcccag acaattcaga attaaatacg     360
acgttactct tgaaaggaga gtttgatcta ttagccgtta attgctttgc ttttggtgaa     420
ggatggaaat ttgcttttgc aaaaaattct gaccttccca cctcaacatt caaaaaatac     480
acagaagaac aaaggaaaca acttattgcc tcactgattc ctgtaacttg gccaccaaag     540
ccaccattca gtgatgaccc attccacctt ctggacgaga tgattgcagc gccagaagag     600
gaaccggtga tagaagaaag tagtgaatta aaagaagtaa agaagatat  agatgtagtt     660
aaagtgaaat cataa                                                      675
```

<210> SEQ ID NO 10
<211> LENGTH: 224
<212> TYPE: PRT
<213> ORGANISM: unknown
<220> FEATURE:
<223> OTHER INFORMATION: encoded amino acid sequence of Sbo13I restriction endonuclease

<400> SEQUENCE: 10

```
Met Arg Glu Pro Ser Ile Leu Glu Arg Trp Glu Ile Ser Glu Glu Lys
1               5                   10                  15

Leu Thr Asp Leu Val Asp Lys Asn Pro Ser Leu Arg Gly Met Ile Leu
                20                  25                  30

Gly Tyr Val Ala Glu Asp Lys Phe His Glu Leu Phe Leu Glu Asp Glu
            35                  40                  45

Arg Val Lys Glu Val Ser Lys Asp Asp His Asp Arg Lys Lys Lys
        50                  55                  60

Gly Asp Arg Thr Phe Ile Tyr Lys Gly Lys Lys Phe Thr Val Glu Val
65                  70                  75                  80

Lys Ser Leu Gln Thr Ala Met Cys Lys Lys Asn Glu Asp Gly Thr Tyr
                85                  90                  95

Ser Gly Lys Ala Gln Val Asp Gly Ser Asp Arg Arg Ile Val Lys Phe
            100                 105                 110

Pro Asp Asn Ser Glu Leu Asn Thr Thr Leu Leu Lys Gly Glu Phe
        115                 120                 125

Asp Leu Leu Ala Val Asn Cys Phe Ala Phe Gly Glu Gly Trp Lys Phe
130                 135                 140

Ala Phe Ala Lys Asn Ser Asp Leu Pro Thr Ser Thr Phe Lys Lys Tyr
```

```
                145                 150                 155                 160
Thr Glu Glu Gln Arg Lys Gln Leu Ile Ala Ser Leu Ile Pro Val Thr
                    165                 170                 175
Trp Pro Pro Lys Pro Pro Phe Ser Asp Asp Pro Phe His Leu Leu Asp
                180                 185                 190
Glu Met Ile Ala Ala Pro Glu Glu Pro Val Ile Glu Glu Ser Ser
            195                 200                 205
Glu Leu Lys Glu Val Lys Glu Asp Ile Asp Val Val Lys Val Lys Ser
        210                 215                 220

<210> SEQ ID NO 11
<211> LENGTH: 21
<212> TYPE: PRT
<213> ORGANISM: unknown
<220> FEATURE:
<223> OTHER INFORMATION: protein sequence of N-terminus of native NruI
<220> FEATURE:
<221> NAME/KEY: MISC_FEATURE
<222> LOCATION: (7)..(7)
<223> OTHER INFORMATION: X = unidentified amino acid residue

<400> SEQUENCE: 11

Met Gly Phe Leu Ala Asp Xaa Asp Leu Ser Tyr Asp Glu Ile Asn Glu
1               5                   10                  15
Leu Leu Thr Asp Asn
            20

<210> SEQ ID NO 12
<211> LENGTH: 17
<212> TYPE: DNA
<213> ORGANISM: unknown
<220> FEATURE:
<223> OTHER INFORMATION: primer
<220> FEATURE:
<221> NAME/KEY: misc_feature
<222> LOCATION: (1)..(1)
<223> OTHER INFORMATION: r = g or a
<220> FEATURE:
<221> NAME/KEY: misc_feature
<222> LOCATION: (4)..(4)
<223> OTHER INFORMATION: n = a, t, c or g
<220> FEATURE:
<221> NAME/KEY: misc_feature
<222> LOCATION: (7)..(7)
<223> OTHER INFORMATION: y = t or c
<220> FEATURE:
<221> NAME/KEY: misc_feature
<222> LOCATION: (10)..(10)
<223> OTHER INFORMATION: r = a or g
<220> FEATURE:
<221> NAME/KEY: misc_feature
<222> LOCATION: (13)..(13)
<223> OTHER INFORMATION: n = a, t, c or g

<400> SEQUENCE: 12
rtcngcyaar aanccca                                                17

<210> SEQ ID NO 13
<211> LENGTH: 17
<212> TYPE: DNA
<213> ORGANISM: unknown
<220> FEATURE:
<223> OTHER INFORMATION: primer
<220> FEATURE:
<221> NAME/KEY: misc_feature
<222> LOCATION: (1)..(1)
<223> OTHER INFORMATION: r = a or g
<220> FEATURE:
<221> NAME/KEY: misc_feature
<222> LOCATION: (4)..(4)
```

```
<223> OTHER INFORMATION: n = a, t, c or g
<220> FEATURE:
<221> NAME/KEY: misc_feature
<222> LOCATION: (7)..(7)
<223> OTHER INFORMATION: n = a, t, c or g
<220> FEATURE:
<221> NAME/KEY: misc_feature
<222> LOCATION: (13)..(13)
<223> OTHER INFORMATION: n = a, t, c or g

<400> SEQUENCE: 13
rtcngcnagt aanccca                                                    17

<210> SEQ ID NO 14
<211> LENGTH: 17
<212> TYPE: DNA
<213> ORGANISM: unknown
<220> FEATURE:
<223> OTHER INFORMATION: primer
<220> FEATURE:
<221> NAME/KEY: misc_feature
<222> LOCATION: (3)..(3)
<223> OTHER INFORMATION: y = t or c
<220> FEATURE:
<221> NAME/KEY: misc_feature
<222> LOCATION: (6)..(6)
<223> OTHER INFORMATION: y = t or c
<220> FEATURE:
<221> NAME/KEY: misc_feature
<222> LOCATION: (9)..(9)
<223> OTHER INFORMATION: r = a or g
<220> FEATURE:
<221> NAME/KEY: misc_feature
<222> LOCATION: (12)..(12)
<223> OTHER INFORMATION: h = a, t or c
<220> FEATURE:
<221> NAME/KEY: misc_feature
<222> LOCATION: (15)..(15)
<223> OTHER INFORMATION: y = t or c

<400> SEQUENCE: 14
taygaygara thaayga                                                    17

<210> SEQ ID NO 15
<211> LENGTH: 21
<212> TYPE: PRT
<213> ORGANISM: unknown
<220> FEATURE:
<223> OTHER INFORMATION: amino acid sequence of N-terminal of translated
      nruIR gene
<220> FEATURE:
<221> NAME/KEY: MISC_FEATURE
<222> LOCATION: (7)..(7)
<223> OTHER INFORMATION: X = unidentified amino acid residue

<400> SEQUENCE: 15

Met Gly Phe Leu Ala Asp Xaa Asp Leu Ser Tyr Asp Glu Ile Asn Glu
1               5                   10                  15
Leu Leu Thr Asp Asn
            20

<210> SEQ ID NO 16
<211> LENGTH: 54
<212> TYPE: DNA
<213> ORGANISM: unknown
<220> FEATURE:
<223> OTHER INFORMATION: primer

<400> SEQUENCE: 16
ggtggtggat ccggaggtaa ataaatggtg attttagcag atattaaaat agac          54
```

```
<210> SEQ ID NO 17
<211> LENGTH: 42
<212> TYPE: DNA
<213> ORGANISM: unknown
<220> FEATURE:
<223> OTHER INFORMATION: primer

<400> SEQUENCE: 17
ggtggtgtcg actcataacg ttttcttctt tcttttcttt tc                42

<210> SEQ ID NO 18
<211> LENGTH: 48
<212> TYPE: DNA
<213> ORGANISM: unknown
<220> FEATURE:
<223> OTHER INFORMATION: primer

<400> SEQUENCE: 18
ggtggtctgc agggaggtaa ataaatggga tttcttgaag actgggac          48

<210> SEQ ID NO 19
<211> LENGTH: 36
<212> TYPE: DNA
<213> ORGANISM: unknown
<220> FEATURE:
<223> OTHER INFORMATION: primer

<400> SEQUENCE: 19
ggtggtggta cctcactctt cgtcttcgat gatctt                       36
```